United States Patent [19]

Heady

[11] 4,356,262

[45] Oct. 26, 1982

[54] PROCESS FOR THE PRODUCTION OF HIGH FRUCTOSE SYRUPS AND ETHANOL

[75] Inventor: Robert E. Heady, Park Forest, Ill.

[73] Assignee: CPC International Inc., Englewood Cliffs, N.J.

[21] Appl. No.: 156,134

[22] Filed: Jun. 3, 1980

[51] Int. Cl.$^3$ .................. C12P 7/06; C12P 19/04; C12P 19/02

[52] U.S. Cl. .................................. 435/97; 435/101; 435/105; 435/161; 435/813; 435/911; 435/940; 435/942

[58] Field of Search .............. 435/94, 97, 105, 101, 435/161, 162, 813, 911, 942, 940

[56] References Cited

U.S. PATENT DOCUMENTS 3,990,944  11/1976  Gauss et al. .................. 435/165
4,077,842  3/1978   Cory .............................. 435/188
4,276,379  6/1981   Heady ........................... 435/94

FOREIGN PATENT DOCUMENTS 2000144  1/1979  United Kingdom.

OTHER PUBLICATIONS

Lodder, *The Yeasts*, North-Holland Publishing Co., Amsterdam, 575–579 (1970).
*The American Type Culture Collection*, Catalogue of Strains I, 13th Edition, Rockville, Maryland, 354 (1978).

*Primary Examiner*—Esther M. Kepplinger
*Attorney, Agent, or Firm*—Stanley M. Parmerter

[57] ABSTRACT

This invention relates to a 1-step process for the preparation of fructose polymers and ethyl alcohol from sucrose. The fructose polymers are especially useful for production of high fructose syrups.

12 Claims, No Drawings

PROCESS FOR THE PRODUCTION OF HIGH FRUCTOSE SYRUPS AND ETHANOL

FIELD OF THE INVENTION

This invention relates to a process for the simultaneous production of fructose polymers and ethyl alcohol from sucrose. The fructose polymers produced can easily be converted to syrups of high fructose content.

BACKGROUND OF THE INVENTION

Commercial fructose-containing syrups are manufactured by the enzymatic isomerization of glucose obtained from corn-derived starch hydrolyzates. This is usually accomplished in a continuous process which involves contacting the glucose-containing solution with a glucose isomerase enzyme preparation that has been immobilized in some fashion. These procedures give a syrup in which fructose is less than 50%, usually 40-45%, of the total carbohydrate present.

Because fructose is sweeter than either glucose or sucrose, much effort has gone into developing processes for producing syrups in which more than 50% of the carbohydrate is fructose. Typically, these methods have involved chromatographic procedures for separating the fructose from the other carbohydrates contained in syrups derived from sucrose and/or corn. Examples are U.S. Pat. Nos. 4,096,036, 4,022,637 and 3,483,031.

Recently, a novel way to obtain fructose syrup of greater than 50% fructose content was disclosed in British Patent Specification No. 2,000,144. According to that procedure, a sucrose substrate is subjected to the action of a fructosyl transferase enzyme to convert the sucrose to an intermediate syrup containing predominantly fructose polymers and glucose. This syrup, in which the fructose is in polymeric form, is useful as a specialty carbohydrate or it can be further treated to produce fructose syrups of greater than 50% fructose content. About half of the glucose in the intermediate syrup can be isomerized to fructose by means of a glucose isomerase enzyme. Subsequent hydrolysis of this reaction mixture cleaves the fructose polymers to fructose, thereby producing a high fructose syrup containing a major amount of fructose and minor amounts of glucose.

SUMMARY OF THE INVENTION

In accordance with the present invention, there is provided for the first time a process for the simultaneous production of ethyl alcohol and fructose polymers. The process involves contacting a sucrose-containing substrate with a mixture of a fructosyl transferase enzyme and a yeast preparation. Purification of the reaction product by removal of cellular debris (e.g., yeast cells) and ethanol yields a syrup containing the fructose polymers. This syrup is useful as a specialty carbohydrate for sweetener and other applications. It may also be hydrolyzed to yield a syrup whose principal sugar is fructose. The fructose content of the sugars in these syrups is generally higher than 66% (by weight) and ranges up to about 75% and even higher, depending upon the composition of the sucrose substrate and the reaction conditions employed.

The process of this invention is unique in its simplicity. This is readily apparent when it is compared with prior art processes for production of high fructose syrups from corn syrup or sucrose. This process requires no separation from glucose. Rather the glucose is converted by fermentation to an easily separated by-product, ethyl alcohol, by means of a yeast preparation that does not ferment the fructose polymers present. Futhermore, the conversion to fructose polymers and the fermentation of the glucose both occur in one reaction mixture without the isolation of intermediates.

DETAILED DESCRIPTION OF THE INVENTION

For purposes of this specification, the following definitions are provided for the various terms used herein:

1. Glucose and Dextrose

The terms "glucose" and "dextrose" are employed interchangeably in this application to embrace this monosaccharide in any form, in solution or dry.

2. Fructose and Levulose

The terms "fructose" and "levulose" are generally employed interchangeably in the art to refer to the isomer of dextrose that is sweeter than dextrose. Fructose is found in honey and in invert sugar, along with dextrose, and is valuable because of its sweetness. The terms levulose and fructose will be used interchangeably in this specification to refer to this monosaccharide in any form, in solution or dry.

3. High Fructose Syrup

This term as used herein refers to any syrup which contains more than 50% fructose by weight on a dry solids basis. It should be noted that commercial 42% fructose-bearing syrup is generally referred to as high fructose corn syrup, but is not intended to be included in the term as used herein.

4. Sucrose

The term "sucrose" refers to this disaccharide in refined or raw form, in solution or dry, from any sucrose raw material source, e.g., sugar cane or sugar beets. In the practice of this invention, the sucrose starting material is typically employed in aqueous medium.

5. Sucrose-Containing Substrate

The term "sucrose-containing substrate" is used herein to refer to any substrate in which sucrose is the predominant sugar. It includes molasses, turbinadoes, meladura, mixtures of sucrose and invert sugars, mixtures of sucrose and fructose-bearing syrup as well as purified sucrose.

6. Secondary Substrate

The term "secondary substrate" as used herein is the reaction product resulting from subjecting a sucrose-containing substrate to the action of a fructosyl transferase enzyme preparation, as defined herein.

7. Polysaccharide

The term "polysaccharide" is used herein to refer to any saccharide made up of two or more monosaccharide units.

8. Fructose Polymer

The term "fructose polymer" is used herein to refer to any polysaccharide in which the preponderence of monosaccharide units are fructose units.

9. Enzyme Preparation

The term "enzyme preparation" is used herein to refer to any composition of matter that exhibits the desired enzymatic activity. The term is used to refer, for example, to live whole cells, dry cells, cell extracts, refined and concentrated preparations derived from the cells and from culture liquors. The enzyme preparations may be used either in a solution or in an immobilized form in the practice of this invention.

10. Transfructosylation

This term as used herein refers to the transfer of a fructosyl group from a donor, e.g., sucrose, to an acceptor, e.g., polysaccharide.

11. Fructosyl Transferase Enzyme

As used herein, this term refers to any enzyme that catalyzes transfructosylation and includes the enzyme preparation derived from *Pullularia pullulans*, ATCC No. 9348 (synonymous with *Aureobasidium pullulans*). In its preferred embodiments, the fructosyl transferase enzyme preparation of this invention contains the fructosyl transferase enzyme in a purified form, that is, separated from the fermentation culture medium in which it was produced.

12. Fructosyl Transferase Unit

As used herein, one fructosyl transferase unit is defined as the amount of enzyme activity required to produce one micromole of reducing sugar, calculated as glucose, per minute under the following conditions: (a) pH 5.5, (b) temperature 55° C., and (c) substrate concentration at 60 g food-grade sucrose per 100 ml of an aqueous reaction mixture.

Reducing sugar (calculated as glucose) is determined using a "Technicon Autoanalyzer II" (Technicon, Inc., Tarrytown, N.Y.). Analysis is carried out by a conventional alkaline ferricyanide method, *Analytical Biochemistry* 45, No. 2, pp. 517–524 (1972), adapted for use in the "Autoanalyzer II". Unless otherwise designated, enzyme activity determinations are performed by continual monitoring of a reaction mixture consisting of the following composition:

- 7.5 ml of 80% (w/v) aqueous food-grade sucrose solution.
- 2.3 ml 0.1 M citrate buffer pH 5.5.
- 0.2 ml enzyme sample containing that amount of fructosyl transferase enzyme which will produce from 5–25 micrograms of reducing sugar (calculated as glucose) per minute per ml of reaction mixture.

13. Yeast Preparation

The term "yeast preparation" is used herein to refer to any yeast cells capable of converting glucose to ethanol, but which does not hydrolyze fructose polymers or sucrose to any significant degree.

14. High Pressure Liquid Chromatographic Assay

This term as used herein defines a procedure whereby the syrups of the invention are analyzed using high pressure liquid chromatography in accordance with the following technique. Components are chromatographed by elution with water from a cation-exchange resin in the calcium form. Eluted components are detected by means of a differential refractometer. All carbohydrates are quantitated using an electronic integrator. The general procedure is that given in "Analysis of Carbohydrate Mixtures by Liquid Chromatography", *Am. Soc. Brew. Chem. Proc.*, 1973, pp. 43–46. The resin used is AMINEX 50W-X4 (20–30μ) in the calcium form, Bio-Rad Laboratories, Richmond, Calif.

The yeast used to carry out the process of this invention may be any one capable of fermenting glucose to alcohol, but which does not hydrolyze fructose polymers or sucrose to any significant degree. Ideally, the yeast strain most suited for this process will be osmophilic, alcohol tolerant, invertase free, lysis resistant, homofermentative and possess cell longevity. It can be a yeast with these characteristics found in nature or a yeast modified by mutation or genetic modification until it possesses the required characteristics. Any yeast of the genus Saccharomyces, which does not produce invertase enzymes, is generally useful. The yeast *Saccharomyces bailii*, ATCC No. 28166, is an example. The yeast *Saccharomyces cerevisiae*, ATCC No. 20597, which is an efficient producer of alcohol from glucose, is particularly suitable.

The yeast preparation used for the process of this invention may consist of yeast cells in either their growth or resting phase as long as they are capable of fermenting monosaccharides to ethyl alcohol. The concentration of yeast cells used to carry out the fermentation may vary over a wide range. However, it is convenient to employ about 1 g of wet cells for every 10 to 20 ml of 35% (w/v) substrate. Wet yeast cells obtained by centrifugation contain about 70–76% moisture.

The fructosyl transferase enzyme preparations preferred for use in this invention may be any enzyme preparations capable of transferring the fructose moiety of sucrose to another molecule of sucrose or to other sugar molecules so that the products are polysaccharides comprising from 2 to about 10 fructosyl units per molecule. Many such enzyme preparations are known. Excellent results have been obtained using the fructosyl transferase enzyme preparations derived from *Pullularia pullulans* such as NRRL No. 3937; ATCC No. 9348; ATCC No. 12535; NRRL No. 1673; NRRL No. Y 2311; NRRL No. YB 3892; ATCC No. 15223; and NRRL No. YB 3861. A procedure for the preparation of the fructosyl transferase enzyme from *Pullularia pullulans* is given in British Patent Specification No. 2,000,144, which is incorporated herein by reference in its entirety. An additional method for its preparation is given in Example 1.

The sucrose-containing substrate used in this invention may be a solution of either refined or raw sucrose. The substrate may also be a mixture of sucrose and varying amounts of other sugars wherein the sucrose content is at least 25% and preferably at least about 50% by weight of the sugars present. Preferred substrates are commercial sources of sucrose such as molasses of varying degrees of purity or mixtures of sucrose with invert sugar. Other useful substrates include meladura, turbinadoes and mixtures of sucrose and fructose-bearing syrups. It is usually a question of economics as to which sucrose source is used. This will depend on the step or steps in the process where purification is most economically achieved.

The fermentation process of this invention is carried out using aqueous solutions of the substrate. Substrate concentrations from as low as about 10% (w/v) may be employed. However, it is preferred to use as concentrated solutions as practical, preferably ranging from about 30% to about 50% (w/v), so that there will be less need to evaporate water from the final product. The reactions are carried out at temperatures of from about 20° C. to about 35° C., preferably from about 24° C. to about 32° C., with the pH of the system from about 4.0 to about 6.5, but preferably from about 5.0 to about 5.5.

The concentration of yeast cells used to carry out the fermentation may vary over a wide range. However, it is convenient to employ about 1 g of wet cells for every 10 to 20 ml of 35% (w/v) substrate. Wet yeast cells obtained by centrifugation contain about 70–76% moisture. The amount of fructosyl transferase enzyme used may also vary widely. A practical rate of reaction is observed when from 10 to 30 fructosyl transferase enzyme units are used per gram of sucrose in the substrate.

The sucrose-containing substrate may be treated concurrently with a fructosyl transferase enzyme and a suitable yeast preparation to carry out the process of this invention. Alternatively, the sucrose-containing substrate may be treated first with a fructosyl transferase enzyme preparation at a suitable temperature, preferably 50°–60° C., for from 3 to 6 hours before the mixture of substrate and fructosyl transferase enzyme is allowed to undergo fermentation with the yeast.

Any conventional means, such as centrifugation or filtration, may be used to remove the yeast cells from the reaction mixture. Recovery of alcohol is most conveniently accomplished by distillation from the fermentation mixture. However, other means such as adsorption may be employed. For example, Ladisch, M. R. and Dyck, K. *Dehydration of Ethanol: New Approach Gives Positive Energy Balance,* In Science. 205: pp. 898–900. Aug. 31, 1979, which is hereby incorporated by reference in its entirety.

If high fructose syrup is desired as a product, the fructose polymers may be hydrolyzed. Hydrolyzing agents and conditions of hydrolysis must be chosen so that the fructose is not destroyed. The reaction may be catalyzed by an acid or an acidic resin. Alternatively, the hydrolysis may be accomplished by means of enzymes such as those contained in commercially available invertase enzyme preparations.

The following examples further describe the embodiments of this invention. All parts are by weight and all percentages are weight by volume (w/v) unless expressly stated to be otherwise.

EXAMPLE 1

Production of Fructosyl Transferase Enzyme

A. The Fermentation Procedure Used to Produce the Enzyme

The medium used for inoculum development and fermentation to produce the enzyme was as follows:
0.5% Dibasic Potassium Phosphate
0.1% Sodium Chloride
0.02% Magnesium Sulfate-Heptahydrate
0.06% Ammonium Sulfate
0.3% Yeast Extract (Difco Labs. Inc., Detroit, Mich.)
6.0% Sucrose (Food Grade)
pH of medium adjusted to 6.8

A first-stage inoculum was prepared as follows. The seed flasks, 500-ml Erlenmeyers containing 100 ml of sterile medium, were inoculated from a slant culture of the black yeast, *Pullularia pullulans*. The particular strain of the yeast employed is designated in the catalogue of the American Type Culture Collection (Rockville, Md.) as ATCC No. 9348. The seed flasks, after development on a reciprocal shaker for 48 hours at 31° C., were used to prepare a second-stage inoculum. This was accomplished by placing 0.25-ml portions of the first-stage inoculum in 25 ml of medium in 250-ml Erlenmeyer flasks. The second-stage inoculum was developed on a reciprocal shaker for 24 hours at 31° C. The entire contents of one flask was used to inoculate a 7.5-liter fermentor containing 5 liters of the medium. The medium was identical with that used for the seed flasks except that the sucrose was at a 12% concentration rather than a 6% concentration, and 0.04% of polypropylene glycol, mol. wt. 2000, antifoam agent was added. The fermentations were carried out at 32° C., with an agitator speed of 500 rpm and with 4 liters of air per minute passing through the mixture. Fermentation was conducted for a total of 65 hours.

B. Recovery of the Enzyme from the Cells

The pH of the fermentor broth was adjusted to 5.5 with 4 N NaOH solution before it was run through a Sharples continuous centrifuge to separate the cells and cellular debris from the supernatant. The wet cells were placed in a 1-liter Erlenmeyer flask with 2 volumes of water. After the addition of 1% toluene and a small amount of Triton X-100 (an alkyl phenoxy polyethoxy ethanol, non-ionic detergent, manufactured by the Rohm & Haas Co., Philadelphia, Pa.), the flask was shaken for 1 hour on a reciprocal shaker to suspend the cells. The flask was then left at room temperature for 3 days with occasional hand mixing. The mixture was filtered through a filter precoated with diatomaceous earth, and the cell cake was washed with water. The filtrate was then concentrated by ultrafiltration through a Pellican Cassette System, manufactured by the Millipore Corp., Bedford, Mass., fitted with a cassette which retains material of greater than 10,000 molecular weight. During the concentration, the retentate was passed through reticulated foam before being returned to the ultrafiltration unit. The retentate was freezedried in a lyophilizer, ground in a mortar and pestle, washed with ethanol, and again lyophilized. The material from 6 such runs weighed a total of 39.9 grams and showed an enzyme activity of 18,976 fructosyl transferase units per gram.

EXAMPLE 2

Preparation of Secondary Substrate

Food-grade sucrose, 4400 g, was dissolved in 4400 ml water. The pH of this solution was adjusted to 5.7 with dilute hydrochloric acid before dosing with 44,000 units of the fructosyl transferase enzyme from Example 1. The solution was incubated at 55° C. for 48 hours. The enzyme reaction was stopped by placing the container in a boiling water bath for 10 minutes. The resulting syrups were shown by analysis to contain 50.38% solids by weight. Carbohydrate composition was determined by high pressure liquid chromatography, with the following results:

Carbohydrate Composition

Fructose: 2.9%
Glucose: 32.9%
Sucrose: 8.2%
1-Kestose: 17.9%
Nystose + Higher Polymers: 36.8%

EXAMPLE 3

Culture of *S. bailii* Yeast

The medium used for inoculum development and fermentation to produce the cells was as follows:
1% Malt Extract
0.2% Ammonium Nitrate
0.2% Dibasic Potassium Phosphate
0.3% Yeast Extract (Difco Labs. Inc., Detroit, Michigan)
15% Secondary Substrate from Example 2
pH of medium adjusted to 5.5

The seed flasks, 500-ml Erlenmeyer containing 100 ml of sterile medium, were inoculated from a slant culture of the yeast, *Saccharomyces bailii*. The particular strain of yeast employed was designated in the catalogue of the American Type Culture Collection (Rockville, Maryland) as ATCC No. 28166. The seed flasks were shaken on a reciprocal shaker for 16 hours at 30° C. before the contents were pooled. To a 1-liter Erlenmeyer fermentation flask, containing 200 ml of the previously defined medium, was added 10 ml of the pooled inoculum. Two such flasks were developed on a reciprocal shaker for 24 hours at 30° C. before the contents were cooled. A 10-ml portion of this second inoculum was used to inoculate a 1-liter Erlenmeyer fermentation flask containing 200 ml of the following medium:
1.0% Malt Extract
0.2% Ammonium Nitrate
0.2% Dibasic Potassium Phosphate
0.3% Yeast Extract (Difco Labs. Inc., Detroit, Michigan)
5.0% Glucose
pH of medium adjusted to 5.5

The fermentation was run at 30° C. on a reciprocal shaker for 24 hours before the broth was run through a Sharples continuous centrifuge to remove the cells. The wet cell pack from 40 such flasks weighed 84.4 grams.

EXAMPLE 4

Isolation and Culture of a Special Strain of *S. cerevisiae* Yeast

Starting Strain

Strain 1453-3A was obtained from the Yeast Genetic Stock Center (Donner Laboratory, University of California, Berkeley, CA 94720). This strain is haploid, mating type a, suc (invertase-less), requires histidine and leucine for growth. It ferments maltose and melibiose.

Mutagenesis

Strain 1453-3A was grown overnight in yeast minimal media (0.67% yeast nitrogen base without amino acids—Difco Laboratories Inc., Detroit, Michigan; 2% glucose and 50 μg/ml of histidine and leucine). Two drops of cell suspension from this culture was spread onto yeast minimal media on agar plates lacking histidine and leucine. After the plates dried, 50 μl of ethylmethane sulfonate was placed on the center of each plate except one which was used as a control. After 8 days at 30° C., 4 colonies were observed on the plates treated with ethylmethane sulfonate whereas no growth was observed on the untreated plate. The 4 putative amino acid revertants were inoculated into glucose minimal media without any histidine or leucine and grown for 36 hours at 30° C. and then frozen at −20° C. in 16.7% sterile glycerol.

Adaptation to Molasses

One of the colonies so obtained was initially inoculated into a rich broth (0.3% yeast extract, 0.3% malt extract and 0.5% bacto-peptone—all from Difco Laboratories Inc., Detroit, Michigan—and 2% glucose). The culture was grown for one week in a reaction vessel maintained at 30° C. with stirring and with the addition of ammonia as needed to keep the pH in the range of 5.2–5.5. The medium was then changed to 21.8% (w/v) molasses containing 0.05% diammonium hydrogen phosphate and 0.1% sulfuric acid. The culture was maintained on this medium for 3 weeks at the above-specified pH and temperature. Upon shutdown, agar plates containing molasses were streaked with the cells and single colonies were inoculated on molasses slants. The invertase-free isolate was found to be very stable and nonreverting. This isolate is on deposit in the American Type Culture Collection and is identified as No. 20597.

EXAMPLE 5

Production of High Fructose Syrup and Ethanol by the Simultaneous Action of Fructosyl Transferase Enzyme and *S. bailii* on Sucrose To 1200 ml of a 30% (w/v) sucrose solution, was added 121.9 g of wet yeast cells produced as in Example 3 and 3600 units of fructosyl transferase enzyme produced by the method of Example 1. The pH was adjusted and maintained at 5.2 by the addition of 0.5 N sodium hydroxide solution as needed. Enzymatic reaction and fermentation were allowed to continue for 23 hours at room temperature before the mixture was filtered through a diatomaceous earth coated filter. The filtrate was heat treated to inactivate the enzyme. Analysis of the mixture by high pressure liquid chromatography indicated the following carbohydrate content:

Carbohydrate Composition

Glucose: 0.8%
Sucrose: 8.6%
1-Kestose: 51.3%
Nystose + Higher Polymers: 38.8%

A small sample of the fermentation mixture, which had been separately centrifuged to remove the yeast cells, was shown by analysis to contain 3.3% (w/v) of ethyl alcohol.

A portion of the filtrate was diluted with water to give a 10% (w/v) solution. This was then hydrolyzed with invertase (Pfanstiehl Laboratories, Waukegan, Illinois) using 0.1 ml of invertase per 10 ml of solution. The solution was covered with a few drops of toluene to inhibit microbial growth and incubated at 32° C. for 48 hours. Carbohydrate content of the resulting syrup, as determined by high pressure liquid chromatography, was found to be 67% fructose and 33% glucose.

This example shows that *S. bailii*, ATCC No. 28,166, in the presence of fructosyl transferase enzyme, can convert sucrose to ethyl alcohol and a mixture of fructose polymers. After removal of the yeast and the alcohol, the fructose polymers in turn may be hydrolyzed directly to a high fructose syrup.

EXAMPLE 6

Production of High Fructose Syrup and Ethanol by the Simultaneous Action of Fructosyl Transferase Enzyme and *S. cerevisiae* on Sucrose To 3.5 liters of 40% (w/v) sucrose solution was added 28,160 units of fructosyl transferase enzyme produced by the method of Example 1 and 176.7 g of wet yeast cells produced as in Example 4. The pH was adjusted and maintained at 5.2 by the addition of 0.5 N sodium hydroxide solution as needed. Enzymatic reaction and fermentation were allowed to continue for 24 hours at 27°–30° C. before the mixture was filtered through a filter precoated with diatomaceous earth. The filtrate was passed through an ultrafilter with a 10,000 molecular weight membrane to remove enzyme. High performance liquid chromatography showed that the syrup had the following carbohydrate composition:

Carbohydrate Composition

Glucose: 5.0%
Fructose: 3.7%
Sucrose: 3.0%
1-Kestose: 26.5%
Nystose+Higher Polymers: 60.4%

The filtrate was shown by high performance liquid chromatography to contain 6.1% (w/v) of ethyl alcohol.

Treatment of a portion of the filtrate with invertase enzyme preparation as in Example 5 converted the syrup to a high fructose syrup which contained 71.3% fructose and 28.0% glucose.

This example shows that *Saccharomyces cerevisiae*, ATCC No. 20597, in the presence of fructosyl transferase enzyme can convert sucrose to alcohol and a fructose polymer, which upon hydrolysis yields a high fructose syrup, in a single reaction mixture without the isolation of intermediate products.

EXAMPLE 7

Production of High Fructose Syrup and Ethanol by the Simultaneous Action of Fructosyl Transferase Enzyme and *S. cerevisiae* on Raw Cane Sugar and Blackstrap Molasses The general reaction of Example 6 was repeated using as substrate a 35% (w/v) solution of a mixture of 10% by weight blackstrap molasses and 90% raw cane sugar. The pH of the reaction was maintained at 5.2 by addition of ammonium hydroxide solution as needed. The yeast cells grew readily in this medium as shown by the increase of $O.D._{650\ nm}$ from 37.6 to 46.6 during the first 12 hours of the fermentation.

The high fructose syrup obtained by invertase treatment after a 24-hour fermentation contained 72.9% fructose and 27.1% glucose.

EXAMPLE 8

Production of High Fructose Syrup and Ethanol by the Simultaneous Action of Fructosyl Transferase Enzyme and *S. bailii* on Secondary Substrate The secondary substrate was prepared by the general procedure of Example 2. Analysis of this secondary substrate showed the following carbohydrate composition:

Carbohydrate Composition

Glucose: 33.4%
Fructose: 2.7%
Sucrose: 7.9%
1-Kestose: 15.4%
Nystose+Higher Polymers: 38.9%

To 1264 ml of 35% (w/v) of the secondary substrate was added 14,747 units of fructosyl transferase enzyme produced by the method of Example 1, and 126.4 g of wet yeast cells produced by the method of Example 3. The pH was maintained at 5.0–5.5 by the addition of 6.5 g of calcium carbonate. The enzymatic reaction and fermentation were allowed to continue for 43 hours at 27°–28° C. A sample was centrifuged for 10 minutes at 18,000 rpm in a refrigerated centrifuge at 1° C. The supernatant was adjusted to pH 8.5–9.0 with 0.5 N sodium carbonate. High performance liquid chromatography showed that the syrup had the following carbohydrate composition:

Carbohydrate Composition

Glucose: 5.1%
Fructose: 3.2%
Sucrose: 2.2%
1-Kestose: 9.0%
Nystose+Higher Polymers: 77.7%

High performance liquid chromatography showed that the syrup contained 4.7% (w/v) of ethyl alcohol.

Treatment of a portion of the syrup with invertase enzyme preparation as in Example 5 converted the material to a high fructose syrup which contained 74.3% fructose and 24.9% glucose.

What is claimed is:

1. A process for the simultaneous production of ethyl alcohol and fructose polymers which comprises contacting a sucrose-containing substrate at a temperature of about 20° C. to about 35° C. and a pH of about 4.0 to about 6.5 with a mixture of an effective amount of fructosyl transferase enzyme and an effective amount of a yeast preparation, that does not hydrolyze sucrose or fructose polymers or ferment fructose polymers, to produce fructose polymers and ethyl alcohol.

2. The process of claim 1 wherein said yeast preparation is a Saccharomyces, said substrate is sucrose and said fructosyl transferase enzyme preparation is obtained from a *Pullularia pullulans*.

3. The process of claim 2 wherein said fructosyl transferase enzyme preparation is derived from *Pullularia pullulans*, ATCC No. 9348.

4. The process of claim 3 wherein said yeast preparation is *Saccharomyces bailli*, ATCC No. 28166, and the reaction is carried out at a temperature of from about 24° C. to about 32° C. and at a pH of from about 5.0 to about 5.5.

5. The process of claim 3 wherein said yeast preparation is *Saccharomyces cerevisiae*, ATCC No. 20597, and the reaction is carried out at a temperature of from about 24° C. to about 32° C. and at a pH of from about 5.0 to about 5.5.

6. The process of claim 1 wherein said fructosyl transferase enzyme preparation is derived from *Pullularia pullulans*, ATCC No. 9348, and said yeast is *Saccharomyces bailii*, ATCC No. 28166, and the reaction is carried out at a temperature of from about 24° C. to about 32° C. and at a pH of about 5.0 to about 5.5.

7. The process of claim 1 wherein said yeast is *Saccharomyces cerevisiae*, ATCC No. 20597, and the reaction is carried out at a temperature of from about 24° C. to about 32° C. and at a pH of about 5.0 to about 5.5.

8. A process for the production of a high fructose syrup and ethyl alcohol which comprises:
   (a) contacting a sucrose-containing substrate at a temperature of about 20° C. to about 35° C. and a pH of about 4.0 to about 6.5 with a mixture of an effective amount of a fructosyl transferase enzyme and an effective amount of a yeast preparation, that does not hydrolyze sucrose or fructose polymers or ferment fructose polymers, to produce a mixture of fructose polymers and ethyl alcohol; and
   (b) treating the resulting mixture with a reagent capable of hydrolyzing polysaccharides to monosaccharides to yield a syrup whose principal sugar is fructose.

9. The process of claim 8 wherein said fructosyl transferase enzyme preparation is derived from *Pullularia pullulans*, ATCC No. 9348.

10. The process of claim 8 wherein the yeast is any *Saccharomyces* which is essentially free of invertase activity.

11. The process of claim 10 wherein the yeast is *Saccharomyces bailii*, ATCC No. 28166, and the reaction is carried out at a temperature of from about 24° C. to about 32° C. and at a pH of from about 5.0 to about 5.5.

12. The process of claim 10 wherein the yeast is *Saccharomyces cerevisiae*, ATCC No. 20597, and the reaction is carried out at a temperature of from about 24° C. to about 32° C. and at a pH of from about 5.0 to about 5.5.

* * * * *